United States Patent [19]

Katayama et al.

[11] Patent Number: 4,814,506
[45] Date of Patent: Mar. 21, 1989

[54] PROCESS FOR PREPARING 3 HALOGENO-2-HYDROXYPROPYLTRIMETHYLAMMONIUM HALIDE

[75] Inventors: Kazuhiko Katayama; Shigeki Hamaguchi, both of Kobe; Yoshikazu Kogame, Takasago; Takehisa Ohashi, Kobe; Kiyoshi Watanabe, Akashi, all of Japan

[73] Assignee: Kanegafuchi Kagaku Kogyo Kabushiki Kaisha, Osaka, Japan

[21] Appl. No.: 88,331

[22] Filed: Aug. 21, 1987

[30] Foreign Application Priority Data

Aug. 26, 1986 [JP] Japan ................................ 61-199513
Jul. 6, 1987 [JP] Japan ................................ 62-168486

[51] Int. Cl.$^4$ ............................................. C07C 85/06
[52] U.S. Cl. ................................... 564/292; 564/296
[58] Field of Search ....................... 564/282, 292, 290; 568/841

[56] References Cited

U.S. PATENT DOCUMENTS 3,135,788  6/1964  Noguchi et al. .................... 562/292
3,721,650  3/1973  DAlelio ................................ 528/73
4,594,452  6/1986  Reimschuessel et al. .......... 564/292
4,709,059  11/1987  Dirlikor et al. .

FOREIGN PATENT DOCUMENTS 60-231632  11/1985  Japan ................................... 564/292

OTHER PUBLICATIONS

Houben–Weyl, Methoden der organischen Chemie, vol. V/3 "Halogenverbindungen", pp. 830–837, George Thieme Verlag.
Baldwin et al., J. Org. Chem., vol. 43, No. 25, pp. 4876–4878 (1978).
Kan et al., Agric. Biol. Chem., 49 (6) 1669–1674 (1985).

*Primary Examiner*—James H. Reamer
*Attorney, Agent, or Firm*—Armstrong, Nikaido, Marmelstein & Kubovcik

[57] ABSTRACT

A process for preparing 3-halogeno-2-hydroxy-propyltrimethylammonium halide or especially one having the (S)-configuration, which comprises reacting 2,3-dihydroxypropyltrimethylammonium halide or one having the (S)-configuration, which is obtained by reacting (R)-3-halogeno-1,2-propanediol with trimethylamine, with a halogenating reagent.

According to the present invention, 3-halogeno-2-hydroxypropyltrimethylammonium halide or one having the (S)-configuration, which is a useful intermediate for the synthesis of carnitine or especially (l)-carnitine, can be obtained economically, efficiently and easily.

4 Claims, No Drawings

PROCESS FOR PREPARING 3 HALOGENO-2-HYDROXYPROPYLTRIMETHYLAMMONIUM HALIDE

BACKGROUND OF THE INVENTION

The present invention relates to a process for preparing 3-halogeno-2-hydroxypropyltrimethylammonium halide having the formula (2):

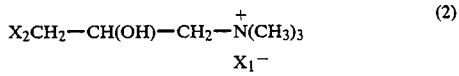

wherein each of $X_1$ and $X_2$ is the same or different halogen atom.

It is known that 3-halogeno-2-hydroxypropyltrimethylammonium halide is a useful intermediate for the synthesis of carnitine and that especially (S)-3-halogeno-2-hydroxypropyltrimethylammonium halide, having the formula (2a):

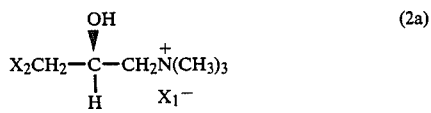

wherein $X_1$ and $X_2$ are as defined above, is a useful intermediate for the synthesis of (l)-carnitine (Japanese Unexamined Patent Publication No. 231632/1985).

(l)-carnitine, which is known as Vitamin $B_T$ and exists widely in a human body, plays an important part as a carrier of a fatty acid having a long chain and also has recently been noticed as the treatment for the carnitine deficiency.

Hitherto, as a method for preparing the compound (2), there has already been known a method for preparing it by reacting epihalohydrin with trimethylammonium halide.

Also, it may be pointed out a method for preparing the compound (2a) by reacting (S)-epihalohydrin with trimethylammonium halide, but is is not easy to prepare (S)-epihalohydrin economically.

There is another method for preparing the compound (2a) from the corresponding racemate (2) by resolution (Japanese Unexamined Patent Publication No. 231632/1985), but this method requires complicated operations to obtain high optical purity of the compound (2a).

Therefore, in preparing (l)-carnitine, the simple and economical method for preparing the compound (2a) is desired.

As the result of the continuous effort of the present inventors in order to find a new method for preparing the compound (2) or (2a) without using epihalohydrin, it is found that 2,3-dihydroxypropyltrimethylammonium halide, having the formula (1):

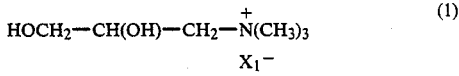

wherein $X_1$ is a halogen atom, or (S)-2,3-dihydroxypropyltrimethylammonium halide, having the formula (1a):

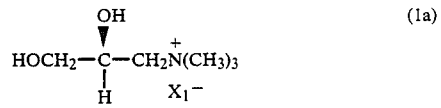

wherein $X_1$ is as defined above can be converted into the corresponding compound (2) or (2a) by the reaction of selective halogenation of the primary hydroxyl group of the compound (1) or (1a) with a halogenating reagent in a high yield.

Consequently, the present invention has been completed.

SUMMARY OF THE INVENTION

According to the present invention, there are provided (A) a process for preparing 3-halogeno-2-hydroxypropyltrimethylammonium halide, having the formula (2):

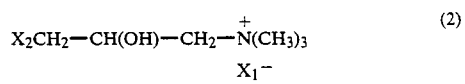

wherein each of $X_1$ and $X_2$ is the same or different halogen atom, which comprises reacting 2,3-dihydroxypropyltrimethylammonium halide, having the formula (1):

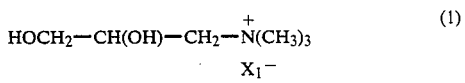

wherein $X_1$ is a halogen atom, with a halogenating reagent, (B) a process for preparing (S)-3-halogeno-2-hydroxypropyltrimethylammonium halide, having the formula (2A):

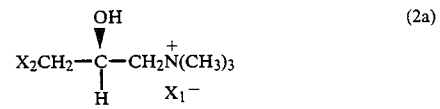

wherein $X_1$ and $X_2$ are defined above, which comprises reacting (R)-3-halogeno-1,2-propanediol, having the formula (3):

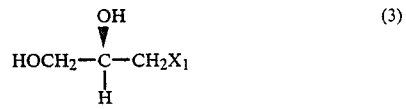

wherein $X_1$ is as defined above, with trimethylamine to form (S)-2,3-dihydroxypropyltrimethylammonium halide, having the formula (1a):

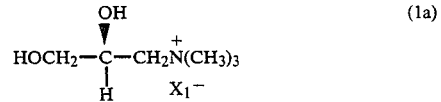

wherein $X_1$ is as defined above, isolating the compound (1a) from the reaction mixture, and reacting the isolated compound (1a) with a halogenating reagent, and (C) a process for preparing the compound (2a), which comprises reacting the compound (3) with trimethylamine in the presence of a dipolar organic solvent to form the compound (1a), without isolating the compound (1a) from the reaction mixture, and reacting the compound (1a) with a halogenating reagent.

DETAILED DESCRIPTION

Hereinafter, the present invention is explained in datail.

Typical examples of 2,3-dihydroxypropyltrimethylammonium halide, having the formula (1), used in the present invention are, for instance, 2,3-dihydroxypropyltrimethylammonium chloride, 2,3-dihydroxypropyltrimethylammonium bromide, 2,3-dihydroxypropyltrimethylammonium iodide and the like. These compounds can be obtained by reacting, respectively, 3-chloro-1,2-propanediol, 3-bromo-1,2-propanediol and 3-iodo-1,2-propanediol with trimethylamine.

(S)-2,3-dihydroxypropyltrimethylammonium halide having the formula (1a) can be easily obtained by reacting (R)-3-halogeno-1,2-propanediol having the formula (3), prepared according to a method as disclosed in Japanese Unexamined Patent Publications Nos. 122596/1987, 122597/1987 and 158494/1987, with trimethylamine.

For instance, (R)-3-chloro-1,2-propanediol is obtained by subjecting (R,S)-3-chloro-1,2-propanediol to the action of microorganism, e.g. *Hansenula anamala* IFO 0707 having an ability of selectively metabolizing (S)-3-chloro-1,2-propanediol, and then by collecting the residual (R)-3-chloro-1,2-propanediol.

(S)-3-halogeno-2-hydroxypropyltrimethylammonium halide having the formula (2a) is used for the synthesis of (l)-carnitine, as shown in the following reaction scheme:

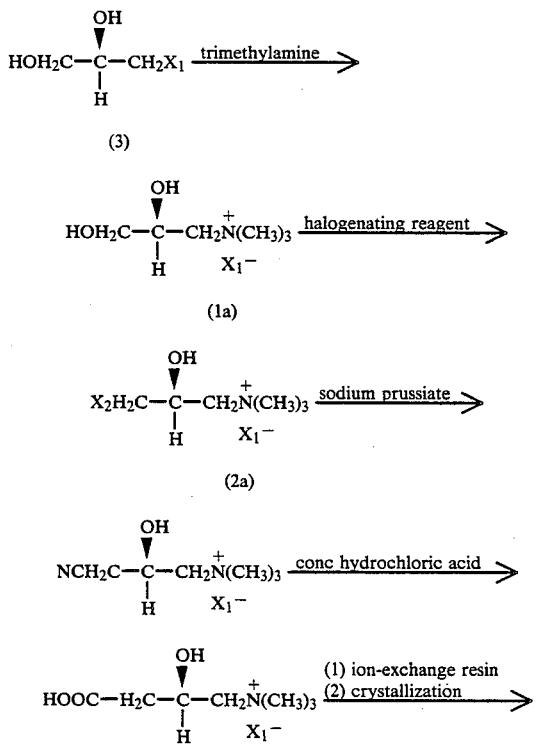

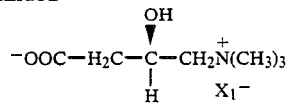

(l)-carnitine wherein $X_1$ and $X_2$ are as defined above.

The compound (1) can be converted in to 3-halogeno-2-hydroxypropyltrimethylammonium halide having the formula (2) by the reaction of selective halogenation of the primary hydroxyl group of the compound (1) with a halogenating reagent in a high yield.

Typical examples of halogenating reagents are thionyl halides such as thionyl chloride and thionyl bromide, phosphorus halides such as phosphorus trichloride, phosphorus tribromide and phosphorus pentachloride, hydrogen halides such as hydrogen bromide and the like.

To the conversion of the compound (1) into the compound (2) by the reaction of halogenation, the reactions of halogenation both by reacting triphenyl phosphate with alkyl halide and by reacting triphenyl phosphine with carborn tetrahalide can be also applied.

Among these halogenating reagents, thionyl chloride and hydrogen bromide are the most suitable agents for chlorination and bromination respectively.

The chlorination by means of thionyl chloride can be carried out in the presence or absence of a solvent. As to the solvents, various kinds of organic solvents, for instance, dipolar organic solvents such as dimethylformamide and dimethylsulfoxide, hydrocarbon halides such as methylene chloride and dichloroethane, aromatic hydrocarbons such as toluene and xylene, hydrocarbons such as n-heptane and octane and the like can be used. And especially, dipolar organic solvents such as dimethylformamide are preferable.

Thionyl chloride may be used in an amount of 1.0 to 3.0 moles per that of 1.0 mole of the compound (1). Preferably, it is used in an excess amount of 5 to 10% by mole to the compound (1), in view of considering isolation and purification after completing of the reaction.

In case of using hydrogen bromide, which is the most suitable reagent for bromination, the reaction of bromination can be carried out by using either hydrogen bromide dissolved in acetic acid or an aqueous solution of hydrogen bromide. Room temperature is a sufficient reaction temperature for the reaction of bromination and the desired 3-bromo-2-hydroxypropyltrimethylammonium halide can be easily obtained as crystals.

The above reaction of halogenation can be carried out at a temperature from 0° C. to the boiling point of used solvent. Because the present reaction is an exothermic reaction, it is preferable to control the temperature so as not to rise suddenly and it is necessary to pay attention in adding a halogenating reagent to the reaction mixture. After adding, the reaction is carried out for 30 minutes to 10 hours at a temperature from 50° to 100° C., and thus the reaction of halogenation is completed.

Both the amount of the compound (2) as a final product and that of the compound (1) as a residue of starting material can be analized by subjecting the reaction mixture to high performance liquid chromatography under the following condition.

Column: Shimpack CLC-ODS (made by Shimazu Seisakusho Co. Ltd.) 15 cm×φ6 mm

Mobile phase: 5 mM NaH$_2$PO$_4$+5 mM H$_3$PO$_4$+200 mM NaClO$_4$,
Flow rate: 1.0 ml/min.
Detector: differential refractometer The primary hydroxyl group of the compound (1a) was also selectively halogenated to give the compound (2a), which is useful for the synthesis of (l)-carnitine. Racemization does not occur during the reaction and the optical purity of the compound (2a) was very high.

Isolation and purification of the compound (2) or (2a) was carried out as follows; concentration, cooling to crystallize and filtration or decantation thereof. Also in order to obtain the compound (2) or (2a) in a high recovery, a method by adding the solvent such as methylene chloride to the reaction mixture to crystallize the desired compound can be employed.

Though the obtained compuond (2) or (2a) is already almost purified and the yield thereof is more than 90% by mole, a further high purity thereof can be obtained, if necessary, by recrystallization from ethanol.

The obtained compound (2) is useful as an intermediate for the synthesis of carnitine.

Also, the compound (2a) is prepared in a high yield according to the process of the present invention, that is, the process which comprises the reaction of the compound (3) as a starting material with trimethylamine to form the compound (1a), isolation of the compound (1a), and then the reaction of the isolated compound (1a) with a halogenating reagent, in the presence or absence of a solvent. Subsequently, (l)-carnitine can be efficiently obtained by the reaction of cyanogenation and then hydrolysis as described in Reference Examples.

Also, dipolar organic solvents such as dimethylformamide and dimethylsulfoxide can be used as a common solvent for the reactions of both trimethylamination and chlorination. Therefore, the compound (2a) can be obtained from the compound (3) in a high yield, without isolating the compound (1a), by using the above solvents.

The present invention is more specifically described and explained by the following Examples and Reference Examples. It is to be understood that the present invention is not limited to the Examples and Reference Examples and various changes and modifications can be made without departing from the scope and spirit of the present invention.

EXAMPLE 1

There was suspended 9.20 g of 2,3-dihydroxypropyltrimethylammonium chloride (chemical purity: 100%) in 50 ml of dimethylformamide, and thereto 6.80 g of thionyl chloride was added at a temperature from 5° to 10° C. After stirring for 20 minutes, it was heated at 100° C. for 5 hours. Finally, after cooling the reaction mixture to room temperature, 9.85 g of 3-chloro-2-hydroxypropyltrimethylammonium chloride was obtained by evaporating the reaction mixture to dryness.

According to the analysis by means of high performance liquid chromatography, the chemical purity thereof was 97% and the yield thereof was 92% by mole.

$^1$H-NMR (D$_2$O, δ(ppm)): 3.8(9H, s, —N(CH$_3$)$_3$), 4 to 4.3 (4H, m, 2×CH$_2$), 4.9 to 5.2 (1H, m, CH).

EXAMPLES 2 To 5

The procedures in Example 1 were repeated except that 2,3-dihydroxypropyltrimethylammonium chloride and thionyl chloride were used in an amount shown in Table 1 and that solvents shown in Table 1 were used in an amount shown in the same table instead of 50 ml of dimethylformamide.

The obtained 3-chloro-2-hydroxypropyltrimethylammonium chloride was analyzed by means of high performance liquid chromatography and thereby the content of it was measured. The results are shown in Table 1 with both the chemical purity thereof (%) and the yield thereof (% by mole).

TABLE 1

| Ex. No. | 2,3-dihydroxy-propyltrimethyl-ammonium chloride (g) | thionyl chloride (g) | solvent and its volume (ml) | 3-chloro-2-hydroxypropyl-trimethylammonium chloride (g) | chemical purity (%) | yield (% by mole) |
| --- | --- | --- | --- | --- | --- | --- |
| 2 | 5.75 | 4.35 | toluene 50 | 6.36 | 100 | 95 |
| 3 | 4.44 | 3.19 | p-xylene 40 | 4.91 | 100 | 95 |
| 4 | 4.37 | 3.18 | n-octane 40 | 4.83 | 100 | 95 |
| 5 | 3.44 | 2.48 | — | 3.70 | 97 | 89 |

EXAMPLE 6

There was added 20 ml of 25 w/v % solution of hydrogen bromide in acetic acid, which had been cooled to 0° C., to 4.00 g of 2,3-dihydroxypropyltrimethylammonium chloride. After stirring for 4 hours at 25° C., the reaction mixture was evaporated to dryness and then was crystallized by adding 40 ml of acetone thereto. Then 3.87 g of 3-bromo-2-hydroxypropyltrimethylammonium salt, which was the mixture of

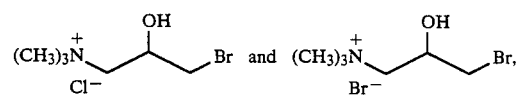

was obtained by filtrating the above obtained crystals.

EXAMPLE 7

The procedures in Example 1 were repeated except that 8.18 g of 2,3-dihydroxypropyltrimethylammonium bromide and 4.78 g of thionyl chloride were used to give 8.43 g of 3-chloro-2-hydroxyprpopyltrimethylammonium bromide.

According to the analysis by means of high performance liquid chromatography, the chemical purity thereof was 95% and the yield thereof was 91% by mole.

$^1$H-NMR (D$_2$O, δ(ppm)): 3.8(9H, s, —N(CH$_3$)$_3$),4 to 4.3(4H, m, 2×CH$_2$), 4.9 to 5.2(1H, m, CH).

EXAMPLE 8

There was added 40 ml of 30 w/v % aqueous solution of trimethylamine to 10.40 g of (R)-3-chloro-1,2-propanediol (optical purity: 100% e.e., chemical purity: 99%). After reacting for 2 hours at room temperature, the reaction mixture was evaporated to dryness to give 15.60 g of (S)-2,3-dihydroxypropyltrimethylammonium chloride as crystals.

According to the analysis by means of high performance liquid chromatography, the chemical purity thereof was 99% and the yield thereof was 98% by mole, and the specific rotatory power thereof was $[\alpha]_D^{25} = -30.8°$ (c=1, $H_2O$).

$^1$H-NMR ($D_2O$, δ(ppm)): 3.4(9H, s, —N($CH_3$)$_3$), 3.5 to 3.8 (4H, m, 2×$CH_2$), 4.1 to 4.5(1H, m, CH).

There was suspended 10.73 g of the obtained (S)-2,3-dihydroxypropyltrimethylammonium chloride in 50 ml of dimethylformamide, and then 7.66 g of thionyl chloride was added thereto at a temperature from 5° to 10° C. After stirring for 20 minutes, it was heated for 5 hours at 100° C. After cooling the reaction mixture to room temperature, the reaction mixture was evaporated to dryness to give 10.56 g of (S)-3-chloro-2-hydroxypropyltrimethylammonium chloride.

$^1$H-NMR($D_2O$, δ(ppm)): 3.8(9H, s, —N($CH_3$)$_3$), 4 to 4.3 (4H, m, 2×$CH_2$), 4.9 to 5.2 (1H, m, CH).

According to the analysis by means of high performance liquid chromatography, the chemical purity thereof was 90% and the yield thereof was 89% by mole. Also, the yield based on (R)-3-chloro-1,2-propanediol was 87% by mole and the specific rotatory power thereof was $[\alpha]_D^{24} = -30.3°$ (c=2, $H_2O$)

EXAMPLE 9

There was added 40 ml of 25 w/v % solution of hydrogen bromide in acetic acid, at 0° C., to 10.30 g of (S)-2,3-dihydroxypropyltrimethylammonium chloride for 4 hours at 25° C. and then the reaction mixture was evaporated to dryness. After 80 ml of acetone was added thereto for crystallization, 10.40 g of (S)-3-bromo-2-hydroxypropyltrimethylammonium salt, which was the mixture of

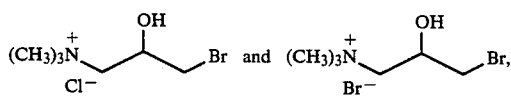

was obtained by filtrating the obtained crystals.

EXAMPLE 10

The procedures in Example 8 were repeated except that 10.73 g of (S)-2,3-dihydroxypropyltrimethylammonium chloride (chemical purity 99%) was suspended in 50 ml of toluene to give 11.25 g of (S)-3-chloro-2-hydroxypropyltrimethylammonium chloride.

According to the analysis by means of high performance liquid chromatography, the chemical purity thereof was 96% and the yield thereof was 91% by mole, and the specific rotatory power thereof was $[\alpha]_D^{24} = -29.0°$ (c=1, $H_2O$).

EXAMPLE 11

There was added 80 ml of 30 w/v % aqueous solution of trimenthylamine to 20.00 g of (R)-3-chloro-1,2-propanediol (optical purity: 100% e.e., chemical purity: 99%). After stirring for 2 hours at room temperature, the reaction mixture was evaporated to dryness to give 30.40 g of (S)-2,3-dihydroxypropyltrimethylammonium chloride.

According to the analysis by means of high performance liquid chromatography, the chemical purity thereof was nearly 100% and the yield thereof was 95% by mole, and the specific rotatory power thereof was $[\alpha]_D^{25} = -30.6°$ (c=1, $H_2O$).

Moreover, the obtained (S)-2,3-dihydroxypropyltrimethylammonium chloride was suspended in 100 ml of dimethylformamide and then 22.57 g of thionyl chloride was added thereto at a tempareture from 5° to 10° C. After stirring for 20 minutes, it was heated for 5 hours at 100° C. Finally, after the reaction was completed and the reaction mixture was cooled to room temperature, it was evaporated to dryness and then the residue was washed with methylene chloride to give 30.20 g of (S)-3-chloro-2-hydroxypropyltrimethylammonium chloride.

According to the analysis by means of high performance liquid chromatography, the chemical purity thereof was 95% and the yield thereof was 93% by mole. Also, the yield based on (R)-3-chloro-1,2-propanediol was 88% by mole and the specific rotatory power thereof was $[\alpha]_D^{24} = -30.1°$ (c=1, $H_2O$).

EXAMPLE 12

There was added 30 ml of 30 w/v % aqueous solution of trimethylamine to 11.05 g of (R)-3-chloro-1,2-propanediol (optical purity: 100% e.e., chemical purity: 99%). After reacting for 2 hours at room temperature, the reaction mixture was concentrated. After dissolving the concentrate in 30 ml of thermal ethanol, the solution was stored over night in a refrigerator. Thus, 15.26 g of (S)-2,3-dihydroxypropyltrimethylammonium chloride was obtained.

According to the analysis by means of high performance liquid chromatography, the chemical purity thereof was 91% and the yield thereof was 90% by mole, and the specific rotatory power thereof was $[\alpha]_D^{25} = -30.8°$ (c=1, $H_2O$).

The obtained (S)-2,3-dihydroxypropyltrimethylammonium chloride was suspended in 20 ml of dimethylformamide and then heated to 100° C. And thereto 11.27 g of thionyl chloride was added dropwise over about 20 minutes, and the reaction mixture was heated for 5 hours at 100° C. for the reaction of chlorination. After cooling the reaction mixture to room temperature, methylene chloride, the volume of which was about ten times as much as the above added dimethylformamide, was added thereto to give a precipitate. After filtration, the precipitate was dried to give 15.82 g of crude product of (S)-3-chloro-2-hydroxypropyltrimethylammonium chloride.

According to the analysis by means of high performance liquid chromatography, the chemical purity thereof was 94% and the yield thereof was 93% by mole. Moreover, the yield based on (R)-3-chloro-1,2-propanediol was 84% by mole and the specific rotatory power thereof was $[\alpha]_D^{24} = -30.7°$ (c=2, $H_2O$).

After 10.00 g of the obtained crude crystals was dissolved in about 100 ml of ethanol, the reaction mixture was subjected to recrystallization by stored over night in a refrigerator to give 7.18 g of white needles thereof as primary crystals.

According to the analysis by means of high performance liquid chromatography, the yield of the obtained primary crystals was 72% by mole and the specific rotatory power thereof was $[\alpha]_D^{24} = -31.1°$ (c=2, H$_2$O).

Repeatedly, the above primary crystals were recrystallized from ethanol. The specific rotatory power of the obtained crystals was $[\alpha]_D^{24} = -31.1°$ (c=2, H$_2$O), which was the same as that of the primary crystals.

EXAMPLE 13

There was added 7.50 g of trimethylamine and 10 ml of dimethylformamide to 11.05 g of (R)-3-chloro-1,2-propanediol (optical purity: 100% e.e., chemical purity: 99%) and then the reaction of trimethylamination was carried out for 50 hours at 60° C. in a 100 ml autoclave.

The reaction mixture was directly poured into a 100 ml three-necked flask. After heated it to 100° C., 11.90 g of thionyl chloride was added dropwise over about 20 minutes. Then, the reaction of chlorination was continued by heating it for 5 hours at 100° C. This reaction was carried out under the open system and hydrogen chloride gas and sulfurous acid gas, both of which were generated during the reaction, were trapped by a concentrated alkali solution.

After cooling it to room temperature, methylene chloride, the volume of which was about five times as much as the above added dimethylformamide, was added thereto to give a precipitate.

After filtration, the precipitate was dried to give 16.31 g of crude (S)-3-chloro-2-hydroxypropyltrimethylammonium chloride.

According to the analysis by means of high performance liquid chromatography, the chemical purity thereof was 95% and the yield based on (R)-3-chloro-1,2-propanediol was 82% by mole and the specific rotatory power thereof was $[\alpha]_D^{24} = -30.6°$ (c=2, H$_2$O).

After 10.00 g of the crude crystals were dissolved in about 100 ml of ethanol, the solution was stored over night in a refrigerator to give 7.02 g of white needles thereof as primary crystals.

According to the analysis by means of high performance liquid chromatography, the yield of the obtained primary crystals was 70% by mole, and the specific rotatory power thereof was $[\alpha]_D^{24} = -31.1°$ (c=2, H$_2$O).

EXAMPLE 14

There was added 7.50 g of trimethylamine and 20 ml of dimethylformamide to 11.05 g of (R)-3-chloro-1,2-propanediol (optical purity: 100% e.e., chemical purity: 99%) and then the reaction of trimethylamination was carried out for 7 hours at 100° C. in a 100 ml autoclave.

The reaction mixture was directly poured into a 100 ml three-necked flask. After heated it to 100° C., 11.90 g of thionyl chloride was added dropwise over about 20 minutes. Then, the reaction of chlorination was continued by heating it for 5 hours at 100° C. This reaction was carried out under the open system and hydrogen chloride gas and sulfurous acid gas, both of which were generated during the reaction, were trapped by a concentrated alkali solution.

After cooling it to 5° C., the crystals were filtered, washed with a little amount of methylene chloride and dried to give 13.50 g of crude (S)-3-chloro-2-hydroxypropyltrimethylammonium chloride as primary crystals.

According to the analysis by means of high performance liquid chromatography, the chemical purity thereof was 99% and the yield based on (R)-3-chloro-1,2-propanediol was 72% by mole and the specific rotatory power thereof was $[\alpha]_D^{24} = -30.7°$ (c=2, H$_2$O).

Moreover, after the above obtained mother liquor was concentrated to about one-third thereof, 2.31 g of (S)-3-chloro-2-hydroxypropyltrimethylammonium choride was obtained as secondary crystals.

According to the analysis by means of high performance liquid chromatography, the chemical purity thereof was 99%, and the secondary yield thereof based on (R)-3-chloro-1,2-propanediol was 12% by mole and the specific rotatory power thereof was $[\alpha]_D^{\cong} = -30.7°$ (c=2, H$_2$O). The total yield of both the primary and the secondary crystals was 84% by mole.

REFERENCE EXAMPLE 1

There was carried out the reaction of cyanogenation by reacting 10.00 g of 3-chloro-2-hydroxypropyltrimethylammonium chloride, which had been obtained in Example 1, with 2.74 g of sodium prussiate to give carnitinonitrile chloride in a yield of 85% by mole.

The above obtained carnitinonitrile chloride was dissolved in 17.50 g of concentrated hydrochloric acid and hydrolized for 2 hours at 100° C. The reaction mixture was evaporated to dryness and again dissolved in 50 ml of water. After it was passed through a 500 ml column of Amberlight (I.R.A.-410 (OH type)), the fraction containing carnitine was dried. The obtained fraction was recrystallized from a solvent mixture of 20 ml of methanol and 30 ml of acetone to give 4.70 g of carnitine.

The data of above obtained carnitine measured by means of NMR spectrum and elementary analysis were the same as those of commercially available carnitine.

REFERENCE EXAMPLE 2

After 10.00 g of 3-bromo-2-hydroxypropyltrimethylammonium salt, which had been obtained in Example 6, was subjected to the reaction of cyanogenation with 2.22 g of sodium prussiate, it was dissolved in 17.50 g of concentrated hydrochloric acid and then hydrolized for 2 hours at 100 ° C. The reaction mixture was evaporated to dryness and again dissolved in 50 ml of water. After it was passed through a 500 ml column of Amberlight (I.R.A.-410 (OH type)), the fraction containing carnitine was dried. The obtained fraction was recrystallized from a solvent mixture of 20 ml of methanol and 30 ml of acetone to give 3.63 g of carnitine.

The data of the above obtained carnitine measured by means of NMR spectrum and elementary analysis were the same as those of commercially available carnitine.

REFERENCE EXAMPLE 3

There was carried out the reaction of cyanogenation by reacting 10.00 g of (S)-3-chloro-2-hydroxypropyltrimethylammonium chloride, which had been obtained in Example 8, with 2.74 g of sodium prussiate to give (R)-carnitinonitrile chloride. The yield thereof was 85% by mole and the specific rotatory power thereof was $[\alpha]_D^{24} = -26.6°$ (c=2, H$_2$O).

Moreover, the above obtained (R)-carnitinonitrile chloride was dissolved in 17.5 g of concentrated hydrochloric acid and hydrolized for 2 hours at 100° C. The reaction mixture was evaporated to dryness and again dissolved in 50 ml of water. After it was passed through a 500 ml column of Amberlight (I.R.A.-410 (OH type)), the fraction containing carnitine was evaporated to dryness.

The obtained fraction was recrystallized from a solvent mixture of 20 ml of methanol and 30 ml of acetone to give 4.51 g of (l)-carnitine.

The specific rotatory power thereof was $[\alpha]_D^{22} = -31.5°$ (c=1, H$_2$O).

REFERENCE EXAMPLE 4

After 10.31 g of (S)-3-bromo-2-hydroxypropyltrimethylammonium salt, which had been obtained in Example 9, was subjected to the reaction of cyanogenation with 2.24 g of sodium prussiate, (R)-carnitinonitrile halide was obtained in a yield of 78% by mole. The above obtained (R)-carnitinonitrile halide was subjected to hydrolysis and ion exchange, according to the method of Reference Example 1, to give 3.50 g of (l)-carnitine.

The specific rotatory power thereof was $[\alpha]_D^{22} = -30.9°$ (c=1, H$_2$O).

In addition to the ingredients used in the Examples, other ingredients can be used in the Examples as set same results.

What we claim is:

1. A process for preparing (S)-3-halogeno-2-hydroxypropyltrimethylammonium halide, having the formula (2a):

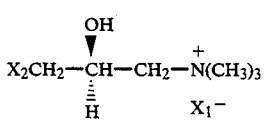

wherein each of X$_1$ and X$_2$ is independently chlorine or bromine atom, which complrises reacting (S)-2,3-dihydroxypropyltrimethylammonium halide, having the formula (1a):

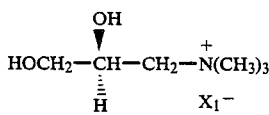

wherein X1 is as defined above, with thionyl chloride or hydrogen bromide.

2. A process for preparing (S)-3-halogeno-2-hydroxypropyltrimethylammonium halide, having the formula (2a):

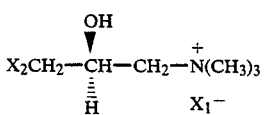

wherein each of X$_1$ and X$_2$ is independently chloride or bromide atom, which comprises reacting (R)-3-halogeno-1,2propanediol, having the formula (3):

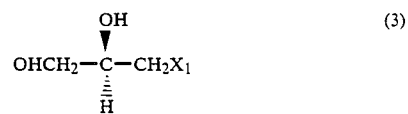

wherein X$_1$ is as defined above, with trimethylamine to form (S)-2,3-dihydroxypropyltrimethylamnonium halide, having the formula

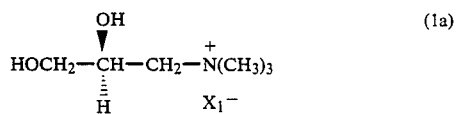

wherein X$_1$ is as defined above, isolating the compound (1a) from the reaction mixture, and reacting the isolated compound (1a) with thionyl chloride or hydrogen bromide.

3. A process for preparing (S)-3-halogeno-2-hydroxypropyltrimethylammonium halide, having the formula (2a):

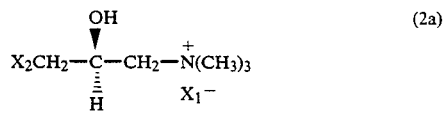

wherein each of X$_1$ and X$_2$ is independently chlorine or bromine atom, which comprises reacting (R)-3-halogeno-1,2-propanediol, having the formula (3):

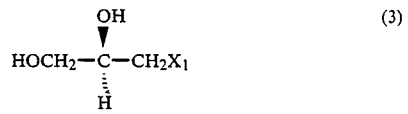

wherein X$_1$ is as defined above, with trimethylamine in the presence of a dipolar organic solvent to form (S)-2,3-dihydroxypropyltrimethylammonium halide, having the formula (1a):

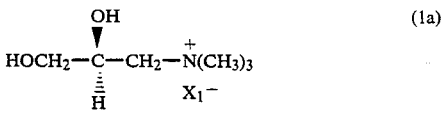

and, without isolating the compound (1a) from the reaction mixture, reacting the compound (1a) with thionyl chloride.

4. The process of claim 3, wherein said dipolar organic solvent is dimethylformamide.

* * * * *